United States Patent [19]

Breidenthal et al.

[11] Patent Number: 4,608,979

[45] Date of Patent: Sep. 2, 1986

[54] APPARATUS FOR THE NONINVASIVE SHOCK FRAGMENTATION OF RENAL CALCULI

[75] Inventors: Robert E. Breidenthal, Seattle; Daniel E. Lotz; David A. Russell, both of Kirkland, all of Wash.

[73] Assignee: Washington Research Foundation, Seattle, Wash.

[21] Appl. No.: 582,271

[22] Filed: Feb. 22, 1984

[51] Int. Cl.$^4$ .............................................. A61B 17/22
[52] U.S. Cl. .................................. 128/303.1; 128/328; 128/369
[58] Field of Search ..................... 128/303.1, 328, 369, 128/370, 395, 396, 397, 398

[56] References Cited

U.S. PATENT DOCUMENTS

| | | |
|---|---|---|
| 3,237,623 | 3/1966 | Gordon . |
| 3,269,173 | 8/1966 | Von Ardenne . |
| 3,392,368 | 2/1968 | Brewer et al. . |
| 3,688,562 | 9/1972 | Munger et al. . |
| 3,715,711 | 2/1973 | Massa . |
| 3,735,764 | 5/1973 | Balev et al. . |
| 3,785,382 | 1/1974 | Schmidt-Kloiber et al. . |
| 3,830,240 | 8/1974 | Antonevich et al. . |
| 3,913,060 | 10/1975 | Westervelt et al. . |
| 3,942,531 | 3/1976 | Hoff et al. . |
| 4,003,383 | 1/1977 | Bruck . |
| 4,034,332 | 7/1977 | Alais . |
| 4,094,306 | 6/1978 | Kossoff . |
| 4,169,662 | 10/1979 | Kaule et al. . |
| 4,178,935 | 12/1979 | Gekhman et al. . |
| 4,191,189 | 3/1980 | Barkan ............................ 128/328 |
| 4,200,858 | 4/1980 | Takashima . |
| 4,309,998 | 1/1982 | Aron et al. . |
| 4,311,147 | 1/1982 | Hausler . |
| 4,336,809 | 6/1982 | Clark ........................ 128/303.1 X |
| 4,396,285 | 8/1983 | Presta et al. ................ 128/303.1 X |

FOREIGN PATENT DOCUMENTS

| | | |
|---|---|---|
| 2351247 | 4/1975 | Fed. Rep. of Germany ... 128/303.1 |
| 2538960 | 4/1977 | Fed. Rep. of Germany ... 128/303.1 |
| 2913251 | 10/1980 | Fed. Rep. of Germany ...... 128/328 |
| 3146626 | 6/1983 | Fed. Rep. of Germany ...... 128/328 |

OTHER PUBLICATIONS

Biomedizinische Technik, vol. 22, No. 7–8, Jul., Aug. 1977; Forssmann et al.; "A method for non-contact destruction of kidney stones . . . " pp. 164–168.
Chaussy, C., Schmiedt, E., Jocham, D., Brendel, W., Forssmann, B., and Walther, V.: "First Clinical Experience With Extracorporeally Induced Destruction of Kidney Stones by Shock Waves", *The Journal of Urology*, vol. 127, Mar. 1982.
Author unknown, "Shattering renal calculi without surgery", *Welcome Trends in Urology*, Nov.–Dec., 1981.

Primary Examiner—Edward M. Coven
Attorney, Agent, or Firm—Christensen, O'Connor, Johnson & Kindness

[57] ABSTRACT

Concretions, such as kidney stones, are nonsurgically fragmented by apparatus which produces focused shock waves. A truncated ellipsoidal reflector is positioned against the patient such that one focus thereof is coincident with the concretion. The reflector is filled with a liquid medium having an acoustical impedance similar to living tissue. A laser beam is focused at the remaining focus, thereby producing a shock wave which is coupled through the liquid medium and the patient's tissue and focused at the concretion. By controlling the energy level and duration of the laser beam, a fragmenting tensile stress is imparted to the concretion.

4 Claims, 8 Drawing Figures

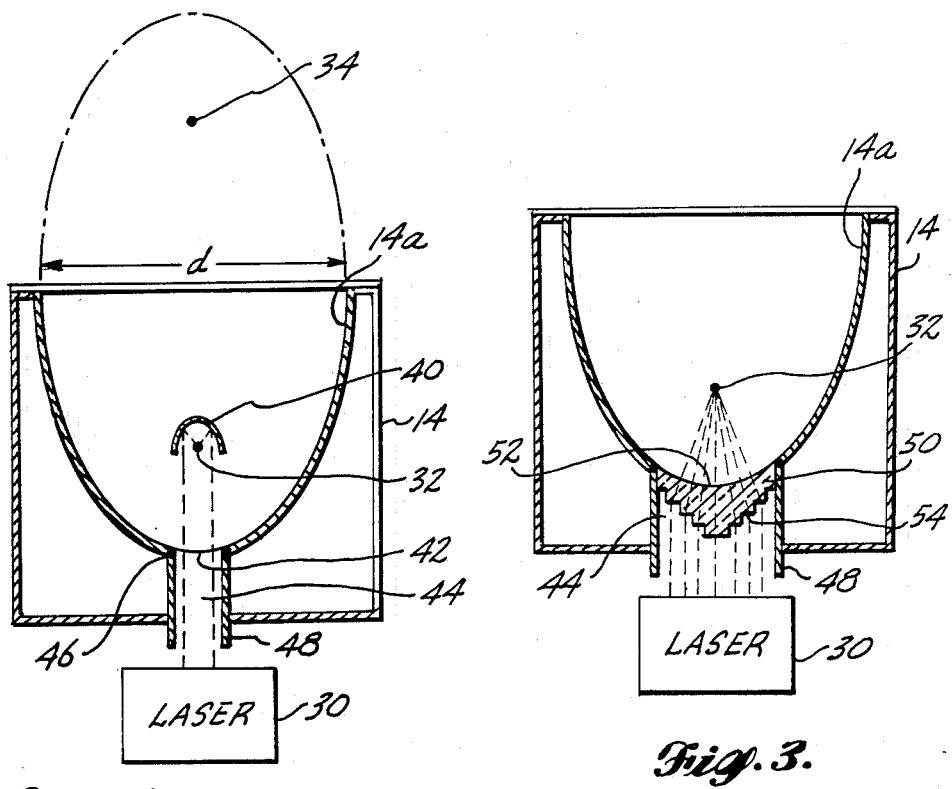
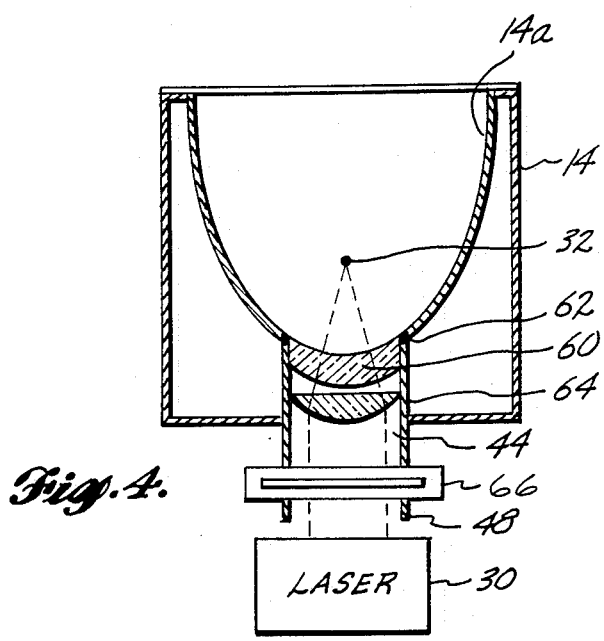
Fig. 2.
Fig. 3.
Fig. 4.

APPARATUS FOR THE NONINVASIVE SHOCK FRAGMENTATION OF RENAL CALCULI

BACKGROUND OF THE INVENTION

The present invention pertains to apparatus for fragmenting kidney stones and other bodily concretions and, more particularly, to apparatus for nonsurgically disintegrating concretions by means of a focused shock wave.

It is estimated that kidney stone disease will affect one percent of the American population at some time in their lives. The disease results from calcium deposits which coagulate into stones (calculi) within the kidney. These stones may then block the ureter causing infection and possible kidney failure. Often, the stones are sufficiently small such that they spontaneously pass through the ureters with varying degree of discomfort. If a stone exceeds one centimeter in diameter, however, in all likelihood it will be too large for passage through the ureter, whereby treatment is required.

Heretofore, the principal method for treating kidney and bladder stones has been by surgical removal.

Kidney stones are commonly composed of calcium compounds and are brittle, comparable to porous ceramic with a tensile strength of approximately 1,000 psi. It is notable that the tensile strength of a stone is approximately one-eighth its compressive strength. This brittle characteristic of the renal calculi has led to the development of apparatus for disintegrating the stones within the body, allowing the fragments to pass from the body during normal elimination.

In one such approach, a lithotriptor is inserted through the urethra into the interior of the body and is positioned into abutting relationship with the bladder or kidney stone to be fragmented. The lithotriptor is connected to a membrane which forms the closing portion of a fluid filled chamber. A high energy spark discharge within the fluid filled chamber creates a shock wave which, when transmitted through the membrane to the lithotriptor, imparts a tensile stress on the stone causing it to shatter.

Although some successful lithotripsy treatments have been reported, there has also been an incidence of bladder wall perforations and shocks to the operators from use of the high voltage equipment. In addition, inasmuch as the procedure is invasive, there are attendant risks involved.

In another approach, the concretions are shattered nonsurgically by use of a shock wave. If a short pressure pulse, such as a shock front, is applied to a stone, the wave will traverse the stone and reflect off the stone/tissue boundary creating a tension stress wave. Due to the brittle nature of the stone, the stress wave, if of sufficient magnitude, will result in stone fragmentation. If the transit time across the stone is less than the pulse width, the momentum in the shock wave is transferred to the stone as a nonfragmenting acceleration. It is essential, therefore, that the shock wave have a controlled, short duration.

In this procedure, the shock wave is focused on the stone by the use of an ellipsoidal waveguide. The waveguide is positioned against the external tissue of the patient's body such that one focal point of the waveguide is coincident with the stone to be treated. Orthogonally positioned X-ray cameras are used to assure proper positioning. The waveguide is filled with a fluid, such as water, and electrodes are positioned at the other ellipsoid focal point. A high energy spark discharged across the electrodes produces a resultant shock wave in the fluid. This shock is reflected off the surfaces of the reflector and through the liquid medium and body tissue to the other reflector focal point, thereby fracturing or fragmenting the stone. The process is repeated until the fragments are sufficiently small such that they may be passed by the body in the normal manner.

Initial studies have indicated that the shock wave employed does not result in tissue or bone damage.

Whereas the shock wave treatment for renal calculi avoids risks incident to surgery, it nonetheless has attendant risks of its own. First, there is the possibility that a current will be passed through the patient at the time of spark discharge and disturb his cardiac pattern. Further, potentially lethal high voltage equipment must be employed to produce the spark discharge. This poses risks to both the patient and the equipment operator. In addition, the spark gap electrodes for use in the aforementioned technique exhibit a short lifetime, resulting in frequent replacement of the electrodes and resultant high cost due to the relatively expensive electrodes which must be employed.

SUMMARY OF THE INVENTION

It is desirable, therefore, to provide apparatus for the nonsurgical fragmentation of concretions utilizing a shock wave generator which does not suffer the deficiencies known to the prior art.

Briefly, according to the invention, apparatus for shock fragmenting a concretion within a living body comprises a waveguide for directing a shock wave produced at a first position within the waveguide to a second position adapted to be aligned with the concretion. The waveguide is adapted to receive a medium for producing a shock wave in the presence of a focused energy beam. A laser produces an energy beam having a predetermined minimum energy level and a predetermined duration. The energy beam is coupled within the waveguide and focused at the aforementioned first position by coupling and focusing means. In use, a shock wave produced by the focused laser energy beam at the first position is directed through the living body to the concretion.

In a preferred construction of the invention, the waveguide is comprised of a truncated ellipsoid having its first focus within the waveguide and its second focus located beyond the truncated extent of the ellipsoid and adapted to be aligned with the concretion.

In one embodiment of the invention, the coupling and focusing means comprises a paraboloid reflector which is positioned within the waveguide such that its focal point is coincident with the aforementioned waveguide first position. A window allows transmission of the energy beam from the exterior to the interior of the waveguide. The window is aligned with the paraboloid reflector such that the laser produced energy beam is focused at the waveguide first position.

In an alternative embodiment of the invention, the coupling and focusing means comprises a Fresnel lens which is mounted in an opening in the waveguide and is configured to focus the energy beam from the laser to the waveguide first position.

In yet a further embodiment of the invention, a transparent window is mounted in an opening provided in the waveguide such that the laser produced energy beam may be transmitted through the window to the interior of the waveguide. A first lens is interposed between the laser and the transparent window and operates to focus the energy beam at the waveguide first position. In addition, a convex mirror is positioned in the path of the energy beam between the laser and the first lens. The energy beam is reflected off of the convex mirror and directed to the first lens, with the convex mirror being configured such that the diameter of the energy beam is predeterminedly increased upon reflection off of the convex mirror thereby increasing the area of the energy beam impinging on the first lens. Further, a second lens may be interposed between the convex mirror and the first lens, with the second lens converting the reflected energy beam from the convex mirror into substantially parallel rays, thereby improving the focus at the first position produced by the first lens.

In yet a further embodiment of the invention, the waveguide may include an acoustic lens which is predeterminedly positioned with respect to the first waveguide position such that a shock wave emanating therefrom is focused at the second waveguide position. The acoustic lens is preferably formed from a material having an acoustic impedance similar to that of the liquid medium received by the waveguide. The acoustic lens may be formed from a material in which the speed of sound is greater than the speed of sound in the liquid medium received by the waveguide. In this event, the acoustic lens has at least one concave focusing surface. For applications wherein the acoustic lens is formed from a material in which the speed of sound is less than the speed of sound in the liquid medium received by the waveguide, the acoustic lens has at least one convex focusing surface.

BRIEF DESCRIPTION OF THE DRAWING

FIG. 2 is a side, cross-sectional view of an ellipsoidal waveguide and illustrates one preferred construction of the invention wherein a laser beam is focused at the first focal point of the waveguide by means of a suitably positioned paraboloid reflector;

FIG. 3 illustrates an alternative construction of the invention wherein the laser beam is focused at the first focus of a paraboloid waveguide by means of a Fresnel lens;

FIG. 4 illustrates an alternative construction of the invention, wherein the laser beam is focused at the first focal point by means of a convex lens;

DETAILED DESCRIPTION

Figure 1:
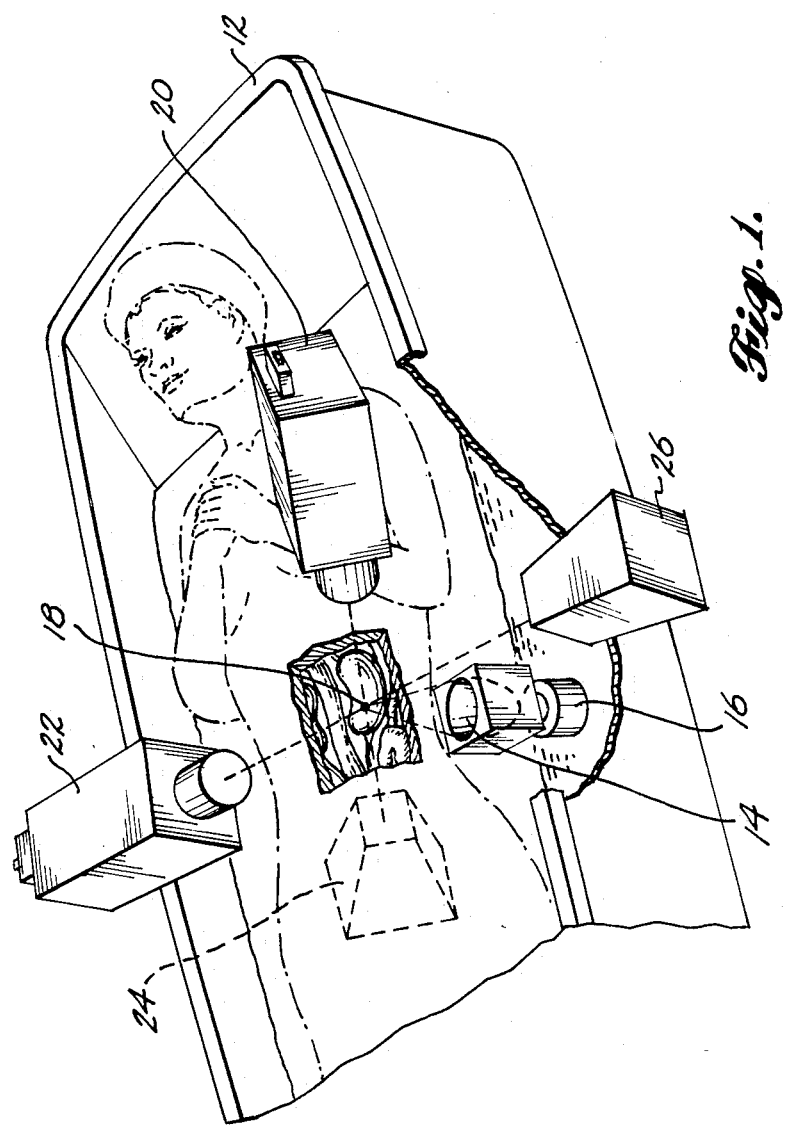
FIG. 1 is a perspective view illustrating the precise positioning of a patient within a fluid filled tub for treatment by the apparatus according to the invention.

In the preferred construction of the invention, a shock wave produced at the first focal point of an ellipsoidal waveguide is directed to the waveguide second focal point which is positioned coincidently with the renal calculus to be fragmented. FIG. 1 illustrates the technique for positioning a patient such that the waveguide second focal point is aligned with the calculus to be treated. Here, the patient is shown reclined within a water filled tub 12. In fixed position within the tub 12 is the ellipsoidal waveguide 14. As discussed in detail hereafter, waveguide 14 is preferably a truncated ellipsoid, having its first focal point contained within the waveguide and its second focal point located at a point beyond the truncated portion. Suitable apparatus 16, described in detail hereafter, produces a focused laser beam at the first focal point of the ellipsoidal waveguide 14, thereby producing a shock wave through rapid vaporization of the liquid medium.

The second focal point of the ellipsoidal waveguide 14 is indicated at a position 18. A pair of orthogonally positioned X-ray machines 20, 22 are aligned with their points of intersection being coincident with position 18. On axis with the X-ray machines 20, 22 are corresponding X-ray sensitive receivers 24, 26, respectively.

The patient is maneuvered within the tub 12 such that the stone to be treated is centered with respect to the beam from both of the X-ray units 20, 22 as monitored by the receivers 24, 26. Inasmuch as the second focal point of the ellipsoidal waveguide 14 is coincident with the intersection of the X-ray beams from the X-ray machines 20, 22, proper positioning of the patient is assured.

Shock waves produced by the apparatus 16 and focused by the ellipsoidal reflector 14 are then directed to the stone at position 18 until X-ray monitoring shows that the stone has fragmented to particles which may be passed by the body in the normal manner.

FIGS. 2–5 illustrate various preferred constructions of the apparatus according to the present invention. In each construction, an energy beam produced by a laser 30 is coupled to an ellipsoidal waveguide 14 and focused at the first focal point of the waveguide 14. While this preferred embodiment of the invention employs an ellipsoidal waveguide, it should be understood that other waveguide shapes, including substantially ellipsoidal configurations, are within the scope of the invention.

The laser 30 used throughout the various embodiments of the invention preferably produces a light beam having an energy of between 1 to 10 joules—a level suitable for fragmenting typical kidney stones. As mentioned hereinabove, the pressure pulse produced by the laser must be of a duration shorter than the wave transit time through the stone such that the incident compression wave produced on the stone reflects at the stone/body tissue interface causing stone fragmentation in a spallation process. Thus, the pulse time for the laser 30 is, preferably, no greater than one microsecond. As a practical matter, lasers are commercially available which produce pulses in the 3–20 nanosecond range. The total number of pulses used per patient is kept to the minimum required to sufficiently fragment the stone and the preferred pulse repetition rate is approximately one pulse per second.

The shock wave produced at the first focal point of the ellipsoidal waveguide 14 is coupled through a liquid medium and through the tissue of the patient to the stone being treated. As such, it is preferable to select the liquid medium from a material having an acoustic impedance similar to that of body tissue. Water has been found to be a suitable liquid medium. Water also serves the second requirement of the liquid medium, namely an optically transparent material which produces a shock wave in the presence of a focused energy beam. While the theory behind the production of a shock wave as a result of a focused laser beam in water is not fully understood, it is thought that the beam strips off electrons from molecules, thereby producing a plasma gas. The suddenly increased volume due to plasma formation impinges on the surrounding fluid resulting in compression waves which propagate outward at the speed of sound. The compression waves nonlinearly reinforce to form a shock wave. The plasma acts as both an absorber and a reflector of incident energy. When the beam is turned off, the plasma relaxes and the electrons recombine to form water vapor.

The wavelength of the energy beam emitted by the laser 30 is selected for minimum absorption in the transmission medium being used. With water chosen as the transmission medium, the laser wavelength is selected for minimum absorption in water. Commonly available absorption data indicates that a low absorption wavelength in water is 1.06 microns. This facilitates the use of a neodymium glass laser. An even lower absorption is realized at 0.503 microns (visible red) which may be produced by passing the neodymium glass laser beam through a nonlinear crystal frequency doubler, thereby producing the desired 0.503 micron wavelength. As a third choice, a ruby laser having a wavelength of 0.694 microns can be used.

Lasers having the required characteristics are commercially available from several sources, including Quantel International, Santa Clara, Calif.

The waveguide 14, as shown in various embodiments of the invention in FIGS. 2-6, is formed from a material exhibiting a high acoustical impedance mismatch with the fluid medium, thereby promoting reflections of the shock waves off of the waveguide/fluid interface. Preferably, the waveguide 14 is formed of brass or aluminum. As shown in cross section in FIG. 2, the waveguide 14 is an aluminum block having machined therein a truncated ellipsoidal inner surface 14a. The first ellipsoidal focal point 32 is located within the waveguide 14, with the second focal point 34 located beyond the truncated extent of the waveguide 14. In the embodiments shown throughout the various constructions of the invention, the inner surface 14a of the waveguide 14 defines one-half of an ellipsoid. The eccentricity of the waveguide 14 is selected to be less than 0.8 and greater than 0.1, inasmuch as experimentation has shown that eccentricities within this range tend to produce the best focus at second focal point 34. As a result of the desired eccentricity and the typical target depth of a concretion within a patient, the waveguide 14 has a cross-sectional diameter d (FIG. 2) at its widest portion of 12.7 centimeters (5 inches).

In the preferred embodiment illustrated in FIG. 2, a paraboloid reflector 40 is positioned within the waveguide 14 such that its focal point is coincident with the first focal point 32 of waveguide 14. Paraboloid reflector 40 is, preferably, a thin aluminized surface on a precision casting or, in the alternative, an electroplated coating on a casting or a precision machined part.

A window 42 is mounted within a bore 44 which extends through the apex of waveguide 14. Window 42 is formed from a material which is transparent to the light beam produced by the laser 30 and which exhibits an acoustic impedance similar to that of the waveguide 14 material, thereby assuring the desired reflection characteristic of the shock waves. A suitable material for window 42 is leaded glass.

The shape of window 42 is such that when mounted in position within bore 44 the inner surface of window 42 continues the ellipsoidal inner surface 14a of waveguide 14. Preferably, window 42 is secured within bore 44 by a compliant O-ring 46. The O-ring 46 acts to both seal fluid within the waveguide 14, and provide a cushioned suspension to window 42, thereby minimizing stress on window 42 from the shock waves.

The window 42 is aligned with the paraboloid reflector 4 such that the light beam produced by the laser 30 may be routed through a pipe 48 which extends into bore 44, through window 42 and to paraboloid reflector 40 to be focused at the first focal point 32, thereby producing the shock wave.

FIG. 3 illustrates an alternative embodiment of the invention, wherein a Fresnel lens 50 is employed. The Fresnel lens 50 is mounted within the waveguide 14 apex bore 44 by means of a compliant seal (such as O-ring seal 46 of FIG. 2) or by cement or other suitable affixing means. The upper surface 52 of Fresnel lens 50 is dished to conform with the ellipsoidal inner surface 14a of waveguide 14. The lower surface 54 of Fresnel lens 50, here shown in cross section, is the conventional Fresnel pattern of a concentric series of simple lens sections. As with window 42 of FIG. 1, Fresnel lens 50 is formed from a material, such as leaded glass, which is transparent to the light beam emitted by the laser 30 and which has an acoustical impedance similar to that of the material used to form waveguide 14.

The light beam emitted by the laser 30 is routed through the pipe 48 to the lower surface 54 of the Fresnel lens 50 whereby it is focused to the first focal point 32 of the ellipsoidal waveguide 14, thereby producing the desired shock wave.

FIG. 4 illustrates yet another embodiment of the invention. Here, a transparent window 60 is mounted within the bore 44 which extends to the apex of the ellipsoidal inner surface 14a of waveguide 14. Window 60 is formed from a material which is transparent to the wavelength of the light beam produced by the laser and which exhibits an acoustical impedance similar to that of the material used to form waveguide 14. As such, window 60 provides a reflecting surface for impinging shock waves. A suitable material for window 60 is leaded glass.

Window 60 is dish-shaped, such that when affixed in position within bore 44, it continues the ellipsoidal inner surface 14a of the waveguide 14. Window 60 has a constant thickness, whereby it does not distort the transmitted light. Preferably, window 60 is mounted in bore 44 by means of a compliant, O-ring seal 62. As with seal 46 of FIG. 2, compliant seal 62 seals the fluid within the waveguide 14 and provides a cushioned suspension for window 60, thereby minimizing damage to window 60 from the impinging acoustic waves.

Also mounted within bore 44 is a planoconvex lens 64 having its flat side closest to the first focal point 32 of the waveguide 14. Planoconvex lens 64 is formed from a material, such as glass, which is transparent to the wavelength of the light beam from laser 30, and is configured to be relatively "fast" having an F/1.0. The focus produced by planoconvex lens 64 is designed to be at the first focal point 32 of the waveguide 14.

The light beam produced by the laser 30 is routed through the tube 48 to the planoconvex lens 64 where it is focused and passed through window 60 to the focal point 32, thereby producing a shock wave in the liquid medium.

It will be noted that the construction of FIG. 4 which utilizes a planoconvex lens is capable of producing a sharper focus, and thus a higher energy concentration than the Fresnel lens 50 of FIG. 3, due to diffraction effects of the Fresnel lens 50.

As mentioned hereinabove, the plasma produced when the laser beam is focused on the liquid medium exhibits both reflection and absorption properties. This reflection property may result in a portion of the laser beam being reflected back through the optics to the laser 30. Such reflected energy may be sufficient to cause damage to components within laser 30. To prevent reflected energy from entering laser 30, a fast optical shutter 66 is interposed in the light path between laser 30 and planoconvex lens 64. Fast optical shutter 66 acts as a means to block reflected light from entering laser 30. The last optical shutter 66 may be either a Pockels cell or a Q-switch. A Pockels cell is an electro-optic light modulator, the operation of which is based on the ability of an applied electric field to produce birefringence ina crystal. The resulting rotation of the polarization permits the transmitted light to vary in intensity with the applied voltage as it passes through polarizers. If such a device is placed within the laser, it operates as a Q-switch, controllably operative to either prevent or allow laser oscillation. A commercial source for these devices is Coherent Components Group, Auburn, Calif.

Whereas the fast optical shutter 66 is shown included in the construction of FIG. 4, it should be understood that such device could be incorporated in any of the several embodiments shown in FIGS. 2–6.

Figure 5:
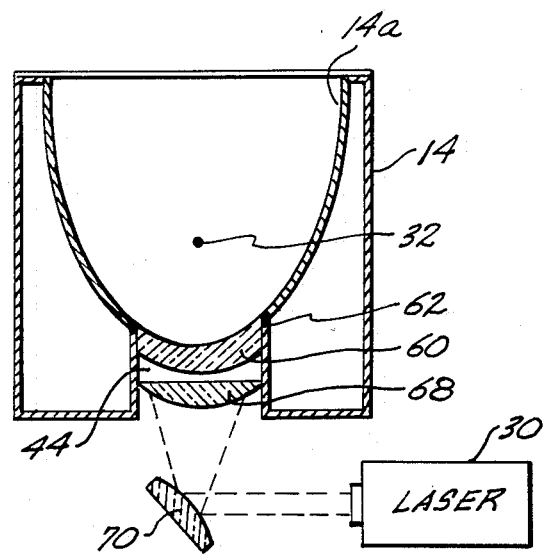
FIG. 5 illustrates a modified form of the configuration of FIG. 3, wherein a convex mirror is used to increase the diameter of the laser beam prior to its being focused by the convex lens.

FIG. 5 illustrates a modified version of the construction shown in FIG. 4. Here, as with the FIG. 4 construction, a window 60 is mounted by means of a compliant seal 62 within a bore 44 in waveguide 14, which bore 44 extends to the apex of the ellipsoidal innersurface 14a. Also mounted within bore 44 is a planoconvex lens 68, having its flat side facing the first focal point 32 of the waveguide 14. Light impinging upon the planoconvex lens 68 is focused through the window 60 to the first focal point 32.

In this embodiment, however, a convex mirror 70 is positioned in the light path between the laser 30, here rotated 90° with respect to the laser position of FIG. 4, and the planoconvex lens 68. In the process of reflecting off the convex surface of mirror 70, the diameter of the light beam from laser 30 increases, thereby spreading out the light beam over a greater surface area of the planoconvex lens 68. This not only tends to reduce spot heating on planoconvex lens 68, but it also allows the use of a "faster" type converging lens 68.

The convex mirror 70 is, preferably, formed by aluminum deposition on a glass lens.

Figure 6:
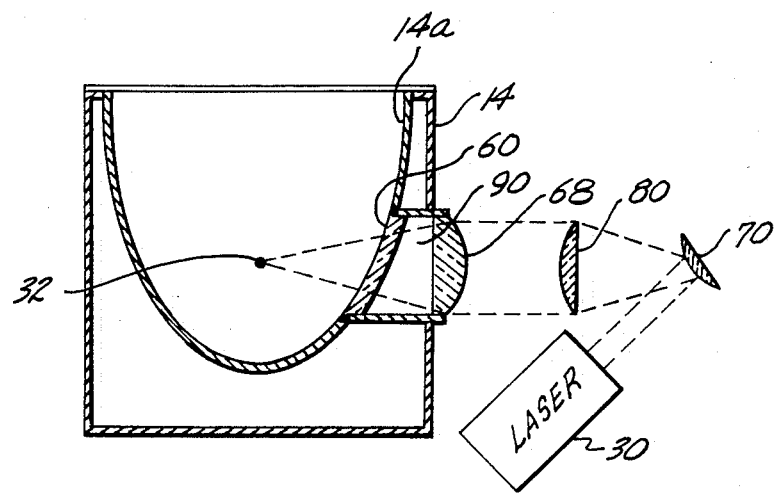
FIG. 6 is yet an improved construction of the embodiment shown in FIG. 5, wherein a second convex lens is interposed between the mirror and the focusing lens to further enhance the resulting focus.

The construction of FIG. 6 is similar to that of FIG. 5 in that the light beam produced by the laser 30 is reflected off of a convex mirror 70, thereby increasing the diameter of the light beam, and then focused through a planoconvex lens 68 and transmitted through a window 60 to the first focal point 32 of the waveguide 14. Here, however, two significant improvements are incorporated. Firstly, a second planoconvex lens 80 is interposed between the convex mirror 70 and the first planoconvex lens 68. The flat side of planoconvex lens 80 faces the light beam reflected off of mirror 70. Thus, the increasing diameter reflected light beam is passed through the second planoconvex lens 80 which is configured to converge the reflected energy beam into substantially parallel rays. In this way, the focus produced by the first planoconvex lens 68 may be significantly improved. As with the first planoconvex lens 68, the second planoconvex lens 80 is selected from a material, such as glass, which is transparent to the wavelength of the light beam emitted by laser 30.

The second difference in the construction of FIG. 6 as compared to that of FIG. 5, is that the transparent window 60 is mounted in a provided bore 90 in the side of waveguide 14. More specifically, the bore 90 is centered on a line extending through the first focal point 32 of the waveguide 14, which line is perpendicular to a line connecting the two focal points of the waveguide 14. As a result of this change, the shape of window 60 has been altered such that it conforms to the side of ellipsoidal inner surface 14a of waveguide 14. As with the construction of FIG. 5, the thickness of window 60 is constant.

Comparing the construction of FIG. 5 to that of FIG. 6, it is seen that the window 60 and planoconvex lens 68 are positioned at a greater distance from the first focal point 32 in the FIG. 6 embodiment. In this way, heating of the window 60 and planoconvex lens 68 is reduced as are reflections from the plasma produced at the first focal point 32 back through to the laser 30, thereby minimizing reflected light induced laser damage.

Figure 7:
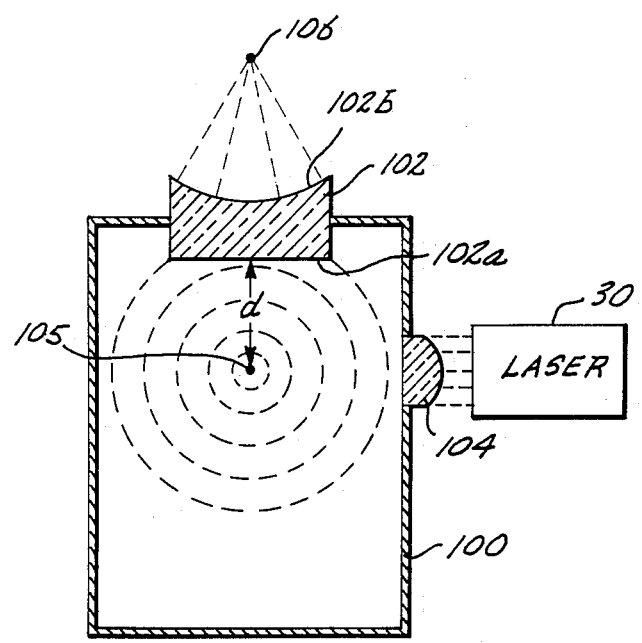
FIG. 7 is a side, cross-sectional view of an alternative embodiment of the invention, wherein a shock wave produced within the waveguide is focused by an acoustic lens having a concave focusing surface.

FIG. 7 is a side, cross-sectional view of an alternative embodiment of the invention which does not employ an ellipsoidal waveguide. Here, a waveguide 100 is generally rectangular in cross section, being an enclosed box in actual construction. Mounted within one end of waveguide 100 is an acoustic lens 102. As shown, acoustic lens 102 is planoconcave, having its concave portion located outside of the waveguide 100.

Mounted within one side of waveguide 100 is a planoconvex focusing lens 104. Light emitted from a laser 30 is focused by planoconvex lens 104 to a first focal point 105 positioned within waveguide 100. Waveguide 100 contains a liquid medium, such as water, which responds to the focused laser beam at focal point 105 to produce shock waves which radiate as concentric circles outwardly from focal point 105. A portion of the shock waves impinge upon the planar surface 102a of acoustic lens 102. The shock waves are then focused, via the concave portion 102b of acoustic lens 102 into a shock wave focused at a second focal point 106. In use, the embodiment shown in FIG. 7 is positioned such that the second focal point 106 is coincident with the concretion to be shattered.

There are several design criteria for the acoustic lens 102. Inasmuch as the liquid medium received within the waveguide 100 has an acoustic impedance similar to the body tissue being treated, the acoustic lens 102 should be formed from a material having an acoustic impedance similar to that of the liquid medium. In this way, reflections of the shock wave off of the planar surface 102a of the lens 102 are minimized, thereby allowing a larger percentage of the energy impinging upon lens 102 to be focused at the second focal point 106. In addition, the acoustic lens 102 must be sufficiently thick, such that it can withstand the force of impinging shock waves without damage. Further, in order to focus impinging shock waves, the acoustic lens 102 must be formed from a material in which the speed of sound is different than the speed of sound in either the liquid medium or body tissue. The embodiment of FIG. 7 which employs a planoconcave lens assumes that the speed of sound in the material from which the acoustic lens 102 is formed is greater than the speed of sound through the liquid medium. A material suitable for use as the acoustic lens 102 in FIG. 7 is commercially known as Lucite.

Figure 8:
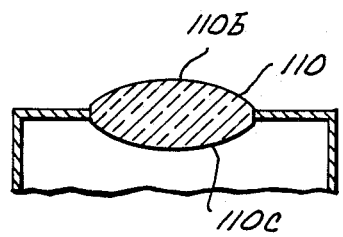
FIG. 8 illustrates an alternative construction of the invention shown in FIG. 7, wherein the focusing lens has compound, convex surfaces.

FIG. 8 illustrates an acoustic lens 110 which may be used in place of the acoustic lens 102 in the embodiment of FIG. 7. Here, acoustic lens 110 is formed from a material in which the speed of sound is less than the speed of sound in the liquid medium or body tissue. As such, the acoustic lens 102 has convex focusing surfaces 110b, 110c.

Returning again to FIG. 7, the distance d between the first focal point 105 and planar surface 102a of acoustic lens 102 should be made as small as possible to maximize the shock wave energy which impinges upon, and is focused by acoustic lens 102. However, this spacing d must be sufficiently large such that the acoustic lens 102 does not suffer damage from impinging shock waves.

In addition, it will be noted that those shock waves which do not impinge upon the planar surface 102a of the acoustic lens 102 travel outwardly and impinge upon the walls of the waveguide 100. Reflections of these shock waves off of the walls might result in secondary shock waves impinging upon the planar surface 102a of the acoustic lens 102, creating other second focal points other than second focal point 106. To minimize such undesirable secondary focal points, the walls of waveguide 100 must be formed of a suitable material, and the spacing from the first focal point 105 to the walls must be such that reflected shock waves back to the acoustic lens 102 are kept at a minimum.

For a lens material such as Lucite, the ratio of sound speed to that in water is approximately 1.8. From the well-known lens maker's formula, the required lens surface radius of curvature is approximately 12 cm for a concave-concave lens. This yields an image distance between the target point 106 and the lens 102 of approximately 15 cm, sufficient range to reach the kidney stone from outside the skin. A plano-concave lens, such as illustrated in FIG. 7, would require roughly half the radius of curvature for surface 102b. The aperture or diameter of the lens should be preferably as large as possible, to collect and focus the maximum amount of energy. For Lucite, a value of 20 cm is desirable.

An improved acoustic lens design is possible over the simple lens maker's formula by using modern ray tracing computer codes, as all modern optical lenses are designed this way.

The dimension d should be comparable to the diameter of the lens, so that the lens captures an appreciable fraction of the energy of the shock wave. For the Lucite example, a good value is 15 cm. The box 100 is lined with acoustic damping material, such as neoprene rubber, if necessary formed into anaechoic wedges to further dampen the reflected waves.

In summary, various preferred embodiments of apparatus for the shock fragmenting of concretions within a living body have been described. By the use of a focused laser beam to produce the shock wave, the present apparatus provides a significant advance in this art over the spark discharge type generators known to the prior art. Inasmuch as no current is passed through the liquid medium by the present apparatus, there is no risk of current through the patient with the possible disturbance of the patient's cardiac pattern. Neither the operator nor the patient are exposed to potentially lethal high voltages. Further, the present construction does not require the constant changing of short lived components, such as spark electrodes.

While preferred embodiments of the invention have been described in detail, it is apparent that many modifications and variations thereto are possible, all of which fall within the true spirit and scope of the invention.

The embodiments of the invention in which an exclusive property or privilege is claimed are defined as follows:

1. Apparatus for use in the shock fragmentation of a concretion within a living body comprising:
    a waveguide having a truncated ellipsoidal inner surface and first and second focal points, said first focal point being located within said waveguide, said second focal point being located beyond the truncated extent of said waveguide and adapted to be aligned with said concretion, said waveguide having a bore extending therethrough, said waveguide being adapted to receive a medium for producing a shock wave in the presence of a focused energy beam;
    laser means for producing an energy beam having a predetermined minimum energy level and a predetermined duration; and
    a lens mounted in the bore of said waveguide adjacent said ellipsoidal inner surface, said lens focusing said energy beam to said first focal point, said lens being reflective of the shock wave produced within said waveguide.

2. The apparatus of claim 1, wherein said lens has an inner surface that conforms substantially with said ellipsoidal inner surface.

3. The apparatus of claim 2, wherein said lens is formed of a material that is transparent to said energy beam and that has an acoustic impedance similar to the acoustic impedance of said waveguide.

4. The apparatus of claim 1, wherein said lens comprises a Fresnel lens.

* * * * *